United States Patent [19]

Fuisz

[11] Patent Number: 4,700,714

[45] Date of Patent: Oct. 20, 1987

[54] URINE COLLECTING DEVICE

[76] Inventor: Richard C. Fuisz, 4146 Green Pond Rd., Bethlehem, Pa. 18017

[21] Appl. No.: 921,833

[22] Filed: Oct. 23, 1986

Related U.S. Application Data

[63] Continuation of Ser. No. 644,442, Aug. 27, 1984, abandoned.

[51] Int. Cl.$^4$ .......................... A61B 5/00; B65D 81/00
[52] U.S. Cl. .................................... 128/767; 128/760; 604/322
[58] Field of Search ............... 604/133, 317, 318, 327, 604/329-331, 345-352, 354, 358; 128/760-762, 767; 4/144.1-144.4

[56] References Cited

U.S. PATENT DOCUMENTS

| | | | |
|---|---|---|---|
| 2,538,758 | 1/1951 | Bricmont | 604/347 |
| 3,403,410 | 10/1968 | Benzel et al. | 604/350 |
| 3,660,033 | 5/1972 | Schwartz | 128/767 |
| 3,858,584 | 1/1975 | Johnson . | |
| 3,918,433 | 11/1975 | Fuisz . | |
| 3,952,729 | 4/1976 | Libman et al. | 604/236 |
| 4,387,726 | 6/1983 | Denard . | |
| 4,453,938 | 6/1984 | Brendling | 604/346 |

Primary Examiner—C. Fred Rosenbaum
Assistant Examiner—Mario Costantino
Attorney, Agent, or Firm—Hopgood, Calimafde, Kalil, Blaustein & Judlowe

[57] ABSTRACT

A predetermined size and shaped piece of dry compressed cellulose sponge is disposed within a compartment formed from plastic sheet material, the compartment being larger than the dry piece of sponge at least in the height or thickness direction, but smaller than the wet expanded piece of sponge at least in the thickness direction so as to limit expansion of the sponge and thereby its liquid uptake to a predetermined quantity. The compartment has an opening in a side wall that communicates with a channel formed in a fan shape panel of the plastic sheet material extending from the compartment, the channel being arranged to conduct urine to the opening when the device is attached to a diaper or other article of clothing and worn with the panel adjacent the genitalia and the compartment adjacent the perineum. A small size embodiment is intended for pediatric use while a larger size device can be used for geriatric care.

9 Claims, 9 Drawing Figures

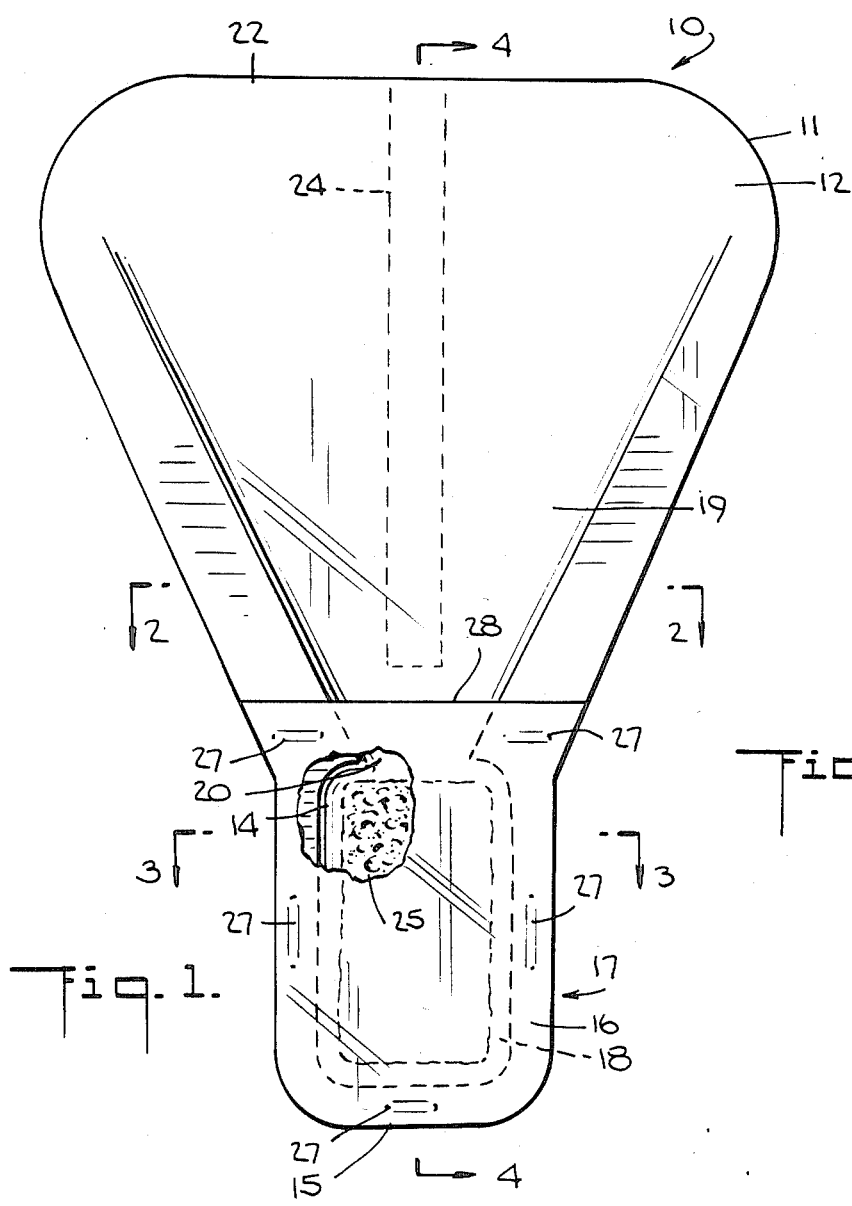
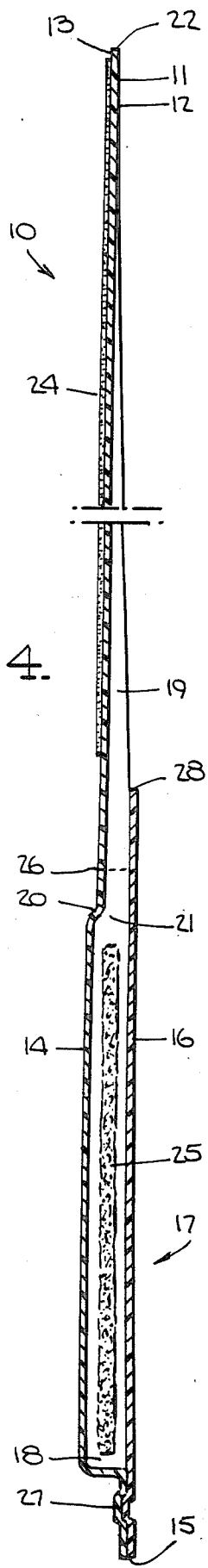
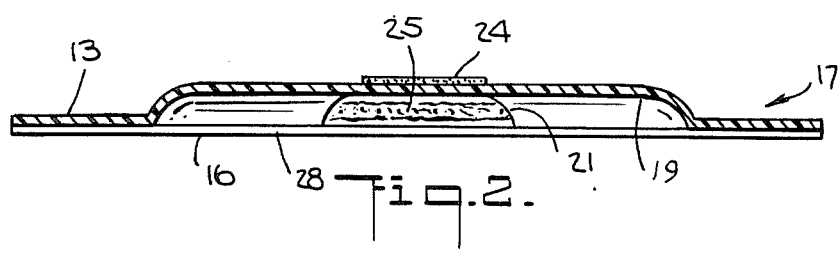
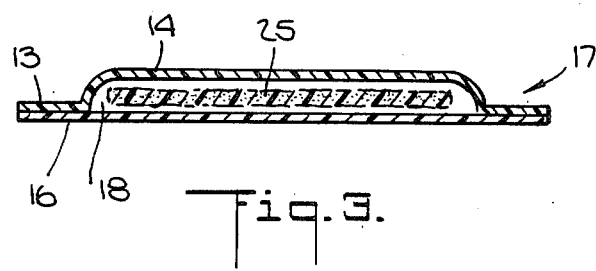

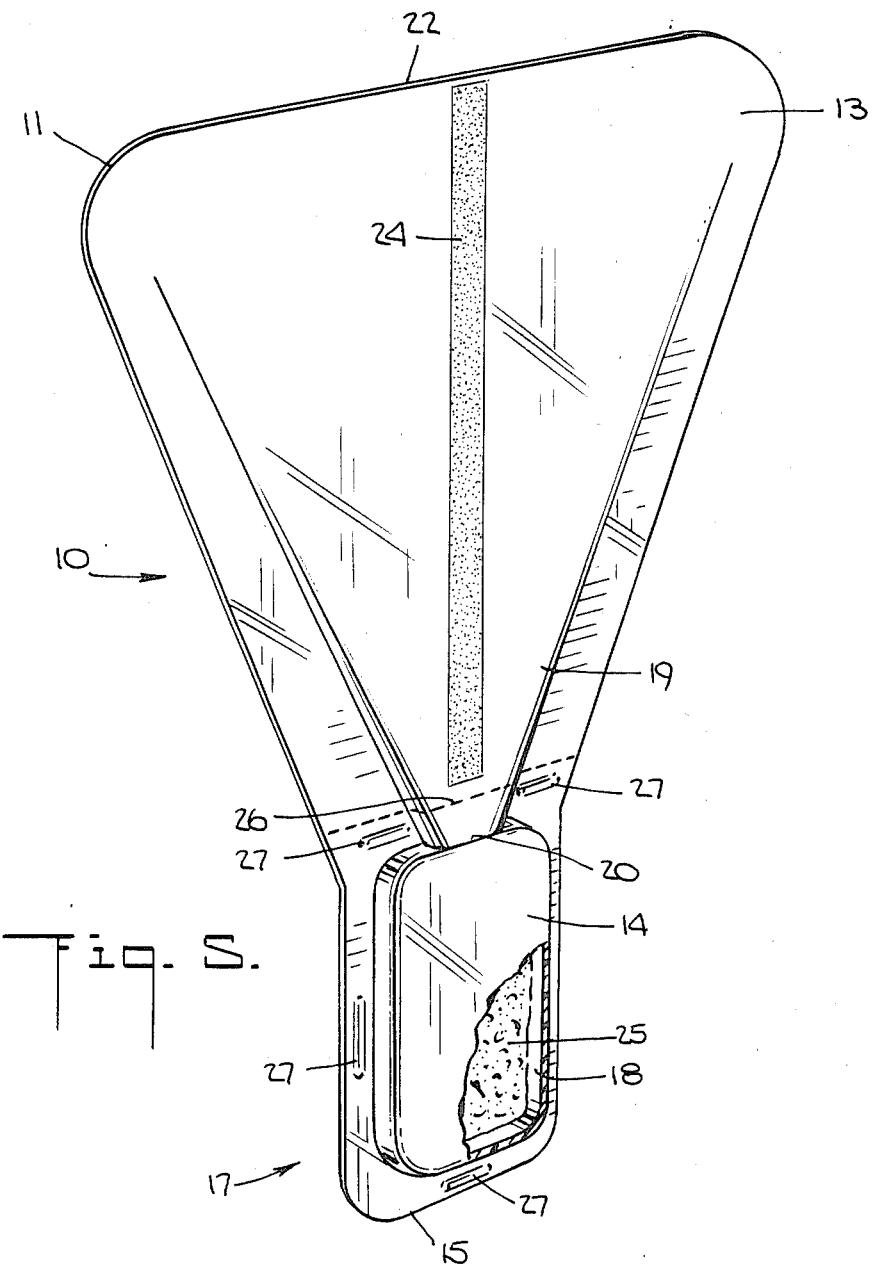
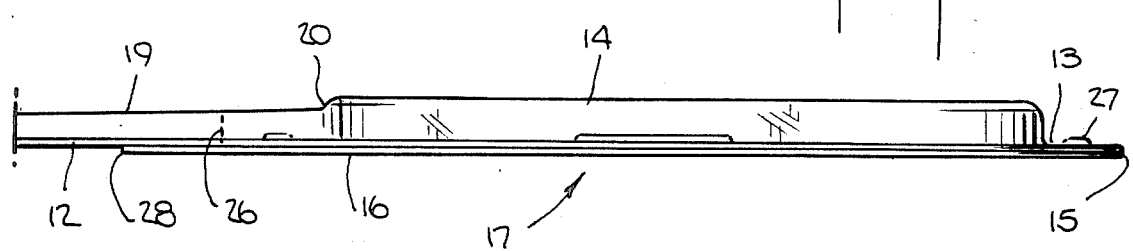

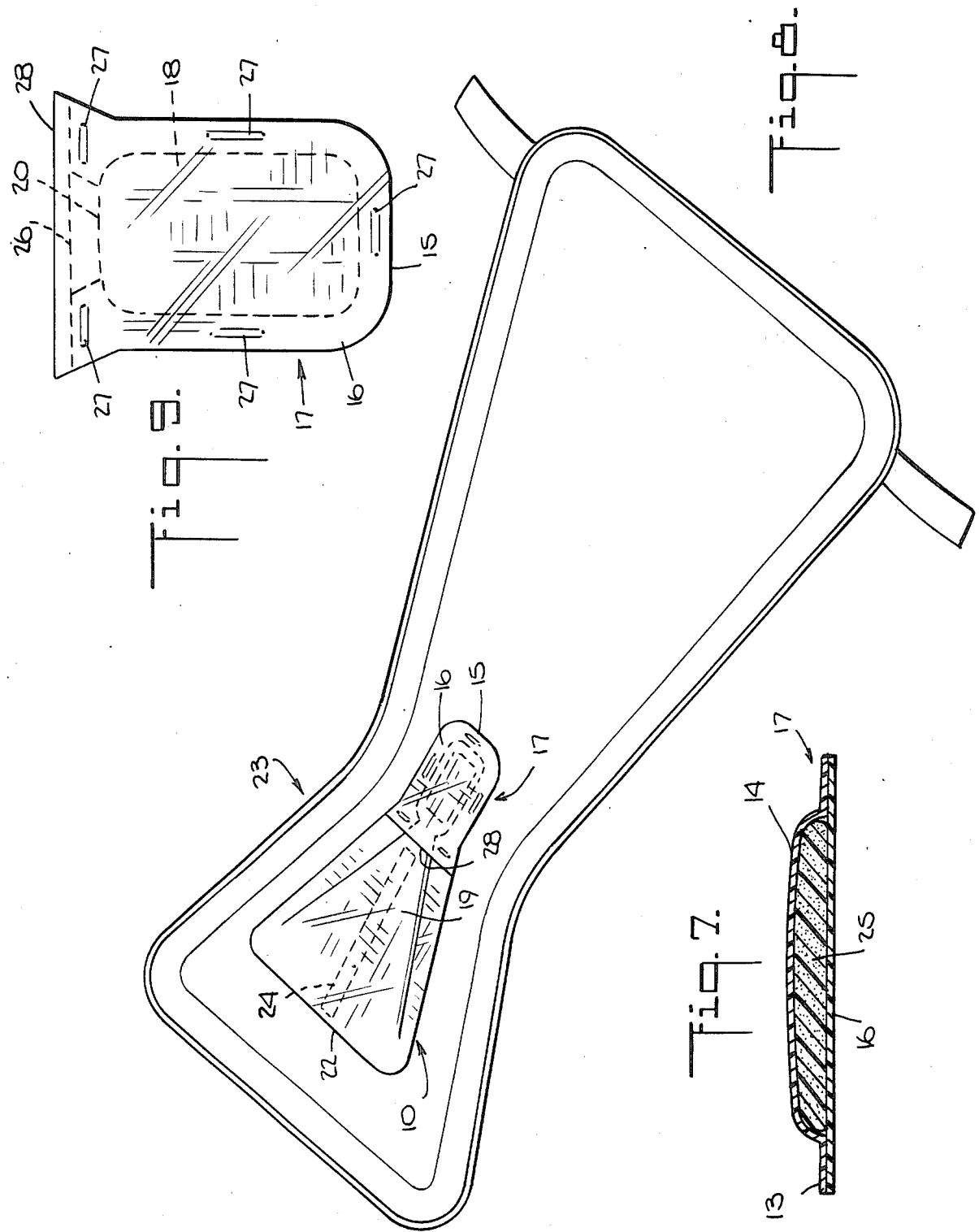

URINE COLLECTING DEVICE

This application is a continuation of application Ser. No. 644,442, filed Aug. 27, 1984, abandoned.

BACKGROUND OF THE INVENTION

The present invention relates to liquid collection devices and more particularly to devices for collecting urine samples.

Urine analysis is a diagnostic tool employed by practitioners of the medical arts providing information bearing upon a wide range of disorders and disease. However, when dealing with infants or incapacitated mature individuals it is difficult to obtain specimens. In both the pre-toilet-trained infant and the senile adult, for example, neither is capable of that control which can provide a specimen on demand.

Various urine sampling devices are available and in my prior U.S. Pat. No. 3,918,433, issued Nov. 11, 1975, and entitled "Fluid Sampling Device", there is described a sampling device, wherein a first surface expanse is provided with channels for conducting urine to a second surface expanse which is associated with a fluid sensitive valve, said second surface expanse leading to a container and said valve being arranged to interpose an occlusive barrier upon the passage therethrough of a predetermined quantity of fluid. Unfortunately, the patented device is unduly complicated and does not lend itself to producing a device that is sufficiently compact.

SUMMARY OF THE INVENTION

It is an object of the present invention to provide a simplified, more versatile, more adaptable, and more advantageous sampling device than those heretofore available.

In accordance with the invention there is provided a urine collecting device having first and second parts for disposition within an article of clothing such that when on the wearer said first and second parts are located adjacent, respectively, the perineum and genitalia, characterized in that said first part comprises an enclosure defining a compartment of predetermined volume, said enclosure having at least one opening for admitting urine to said compartment, and a body of dry compressed absorbent material disposed within said compartment, said body being smaller than said compartment and expandable when wet until constrained by said enclosure, said second part comprising a panel of a liquid impermeable material including at least one channel for guiding urine to said opening, said panel extending from said first part, the relationship between said absorbent body and said compartment being such that said body will absorb a controlled quantity of urine.

BRIEF DESCRIPTION OF THE DRAWINGS

The invention will be better understood after reading the following detailed description of the presently preferred embodiments thereof with reference to the appended drawings in which:

. FIG. 1 is a top plan view of an embodiment of the sampling device in accordance with the present invention;

FIG. 2 is an enlarged transverse sectional view taken along line 2—2 in FIG. 1;

FIG. 3 is an enlarged transverse sectional view taken along line 3—3 in FIG. 1;

FIG. 4 is an enlarged longitudinal sectional view taken along line 4—4 in FIG. 1;

FIG. 5 is a perspective view of the bottom or underside of the device shown in FIG. 1;

FIG. 6 is a fragmentary side elevational view of the device of FIG. 1 with the bottom surface up;

FIG. 7 is a view similar to FIG. 3, but showing the expanded wet sponge in relation to the enclosure;

FIG. 8 is a perspective view showing the device attached to a baby diaper; and

FIG. 9 is a top plan view of the enclosure after separation from the impermeable panel.

The same reference numerals are used throughout the drawings to designate the same or similar parts.

DETAILED DESCRIPTION OF THE PRESENTLY PREFERRED EMBODIMENTS

Referring to the drawings, the urine collecting device is designated generally by the reference numeral 10. The device 10 consists of a generally oblong piece of plastic sheet material 11 having top and bottom surfaces 12 and 13, respectively. The expressions "top" and "bottom" as used herein are intended only for reference purposes and have no other significance.

The sheet 11 is formed relative to the top surface 12 with a depressed region 14 near a first end 15 which region is covered by a substantially flat layer 16 of plastic sheet material to form an enclosure 17 defining a compartment 18 of predetermined volume. Another depressed region 19 is formed in the uncovered portion of the unitary piece 11 relative to the top surface 12 to provide a channel therein which merges in the region 20 with the depressed region 14 thereby providing an opening 21 for the compartment 18 within the enclosure 17.

As seen in the drawings, the enclosure 17 is generally rectangular in plan view with its long dimension coinciding with the long dimension of the oblong piece 11. The uncovered portion of the piece 11 is generally fan shape, as shown, diverging from the short dimension of the enclosure 17 outwardly toward an edge 22 remote from the enclosure 17. The fan shape portion of the piece 11 provides a panel which is intended to overly the general region of the genitalie when worn within an article of clothing such as a diaper. The enclosure portion 17 is configured and dimensioned to fit within the perineum region as will be understood from a consideration of FIG. 8 wherein the device 10 is shown attached to a typical diaper 23 of non-woven fabric.

The material 11 should be impermeable to liquid and may be formed from a thin film or sheet of polyvinyl chloride resin. Sheet 16 may be fabricated from the same material.

A convenient method of securing the device to the inner surface of the diaper 23 involves providing a layer 24 of pressure sensitive adhesive on at least a portion of the bottom surface 13 of the panel 11. As best seen in FIGS. 1, 4 and 5, the layer of adhesive is in the form of a stripe running along the longitudinal axis from the edge 22 toward the vicinity of the area 20. Any convenient pattern may be employed for the adhesive so long as it has the capability of securing the device to the typical layer of liquid permeable plastic material that usually constitutes the inner surface of a diaper 23 as shown in FIG. 8. Such diapers usually have a liquid impermeable outer layer, a liquid permeable inner layer and a filling of a suitable cellulose wadding.

The sampling device is completed by incorporating within the enclosure 17, in the compartment 18, a body 25 of dry compressed absorbent material. The body 25 is smaller than the compartment 18 when the body is dry and is expandable when wet until constrained by the enclosure 17. Thus, as best seen in FIG. 3, there is substantial clearance between the dry body 25 and the compartment 18. While, as shown in FIG. 7, the wet body 25 has expanded until it is constrained by the lesser height of the compartment 18. The body 25 is preferably formed from compressed cellulose sponge.

In an embodiment of the invention intended for pediatric use the compartment 18 may be approximately 1 3/16 inches wide by 2 inches long by 5/16 inches high while the dry sponge may be approximately 1 inch wide by 1¾ inches long by 1/16 inch high. By way of example, it has been found that a body with the foregoing dimensions and of compressed cellulose sponge as furnished by American Sponge and Chamois Co., Inc. of Long Island City, N.Y., will expand when wet in free space to approximately a height or thickness of ⅜ inch. This is in excess of the 5/16 inch height of the compartment 18. Therefore, the constraint of the compartment volume tends to control the quantity of urine that can be absorbed by the sponge body 25 such that approximately the same quantity is absorbed from one sampling device to the next. It has been found that the subject sponge within the specified compartment will absorb approximately 7 cc. of urine.

It is contemplated that the subject sampling device can be made in larger size for use by adult individuals in which case the sponge may be 2 inches wide, 3 inches long and the same 1/16 inch thick when dry and will absorb approximately 23 cc. of urine when wet. This assumes the same 5/16 inch depth compartment to limit the expansion of the sponge. Knowledge of the quantity of urine that can be collected is useful when the sample is intended for laboratory testing of the type requiring a certain minimum quantity.

In order to facilitate handling and laboratory examination the device is provided with a tear line or line of weakening 26 such that the panel portion of the device can be removed from the enclosure 17 leaving the enclosure as shown in FIG. 9.

While any suitable method can be employed to fasten the sheet 16 to the sheet 11, the drawings show the layers joined by zones of spot welding 27. The strength of such welds should be such that the layer 16 can be peeled from the layer 11 by grasping an edge such as 28, to thereby expose the sponge 25 and permit its removal from compartment 18.

Having described the invention with reference to the presently preferred embodiments thereof it will be understood by those skilled in the subject art that various changes in construction and materials may be effected without departing from the true spirit of the invention as defined in the appended claims.

What is claimed is:

1. A urine collecting and sampling device comprising in combination first and second parts for disposition within an article of clothing such that when on the wearer said first and second parts are located adjacent, respectively, the perineum and genitalia, said first part being in the form of an enclosure defining a compartment of predetermined volume with side walls of shallow height, said enclosure being configured and dimensioned to fit within the perineum region and having at least one unobstructed opening in a side wall for admitting urine to said compartment, a body of dry compressed absorbent material smaller than said compartment disposed within said compartment but not otherwise confined therein, said body if unconfined by said compartment being expandable when wet to an uncompressed volume that would exceed said predetermined volume, but when in said compartment said body is able to expand only until constrained by said enclosure, and said second part comprising a panel of liquid impermeable material including at least one channel for guiding urine directly to said opening, for free direct access to said adsorbent body, said panel being joined to and extending from said first part, the relationship between said adsorbent body and said compartment dimensions being such that said body will absorb a controlled quantity of urine.

2. A urine collecting device according to claim 1, wherein a unitary generally oblong piece of plastic sheet material having a top and bottom surface is formed, relative to said top surface, with a depressed region near a first end which region is covered by a substantially flat layer of plastic sheet material, smaller than said unitary piece, to form said enclosure and define said compartment while leaving a portion of said unitary piece uncovered, another depressed region being formed in said uncovered portion of said unitary piece relative to said top surface to provide at least a major portion of said channel, and means are associated with said device for securing it to said article of clothing with said bottom surface contacting said article.

3. A urine collecting device according to claim 2, wherein said compressed absorbent material comprises a piece of compressed cellulose sponge.

4. A urine collecting device according to claim 3, wherein said compartment has a height of about 5/16″, and said body is expandable when wet to a thickness of about ⅜ in the absence of said enclosure restraint.

5. A urine collecting device according to claim 2, wherein a tear line is provided in said oblong piece of plastic transverse to its long dimension generally at the juncture between said enclosure and said uncovered portion of said unitary piece for facilitating separation of said uncovered portion from said enclosure.

6. A urine collecting device according to claim 2, wherein said enclosure is generally rectangular in plan view with its long dimension coinciding with the long dimension of said oblong piece, and said uncovered portion of said unitary piece constitutes said panel and is generally fan shape diverging from the short dimension of said enclosure outwardly toward an edge remote from said enclosure.

7. A urine collecting device according to claim 6, wherein a tear line is provided in said oblong piece of plastic transverse to its long dimension generally at the juncture between said enclosure and said panel for facilitating separation of said panel from said enclosure.

8. A urine collecting device according to claim 1, wherein said compressed absorbent material comprises a thin piece of compressed cellulose sponge dimensioned to fit within a 2″×3″ rectangular space.

9. A urine collecting device according to claim 8, wherein said compartment has a height of about 5/16″, and said body is expandable when wet to a thickness of about ⅜″ in the absence of said enclosure restraint.

* * * * *